(12) United States Patent
Rangaswamy et al.

(10) Patent No.: US 9,260,731 B2
(45) Date of Patent: Feb. 16, 2016

(54) BUTANOL FERMENTATION USING ACID PRETREATED BIOMASS

(75) Inventors: Vidhya Rangaswamy, Navi Mumbai (IN); Jasmine Isar, Navi Mumbai (IN); Harshvardhan Joshi, Navi Mumbai (IN)

(73) Assignee: RELIANCE INDUSTRIES LIMITED, Mumbai, Maharashtra (IN)

( * ) Notice: Subject to any disclaimer, the term of this patent is extended or adjusted under 35 U.S.C. 154(b) by 52 days.

(21) Appl. No.: 14/236,444

(22) PCT Filed: Aug. 1, 2012

(86) PCT No.: PCT/IN2012/000536
§ 371 (c)(1),
(2), (4) Date: Jan. 31, 2014

(87) PCT Pub. No.: WO2013/072919
PCT Pub. Date: May 23, 2013

(65) Prior Publication Data
US 2014/0178955 A1 Jun. 26, 2014

(51) Int. Cl.
*C12N 1/38* (2006.01)
*C12N 1/20* (2006.01)
*C12P 7/16* (2006.01)
*C12N 15/01* (2006.01)
*C12R 1/145* (2006.01)
*C12N 15/74* (2006.01)

(52) U.S. Cl.
CPC ..... *C12P 7/16* (2013.01); *C12N 1/20* (2013.01); *C12N 15/01* (2013.01); *C12N 15/74* (2013.01); *C12R 1/145* (2013.01); *Y02E 50/10* (2013.01)

(58) Field of Classification Search
CPC .......... C12N 1/20; C12N 15/00; C12N 15/01; C12P 7/16
See application file for complete search history.

(56) References Cited

U.S. PATENT DOCUMENTS

| | | | |
|---|---|---|---|
| 4,520,104 A | 5/1985 | Heady et al. | |
| 4,521,516 A | 6/1985 | Lemme et al. | |
| 4,539,293 A | 9/1985 | Bergstrom et al. | |
| 4,560,658 A | 12/1985 | Datta et al. | |
| 4,605,620 A | 8/1986 | Andersch et al. | |
| 4,757,010 A | 7/1988 | Hermann et al. | |
| 4,777,135 A | 10/1988 | Husted et al. | |
| 5,192,673 A | 3/1993 | Jain et al. | |
| 6,358,717 B1 | 3/2002 | Blaschek et al. | |
| 2005/0233031 A1 | 10/2005 | Hughes | |

FOREIGN PATENT DOCUMENTS

| | | |
|---|---|---|
| EP | 0 111 683 A1 | 6/1984 |
| FR | 2 550 222 A1 | 2/1985 |
| JP | 62-278989 | 12/1987 |
| JP | 63-157989 | 6/1988 |
| JP | 63-269988 | 11/1988 |
| JP | 03-058782 | 3/1991 |
| JP | 2005-328801 A | 12/2005 |
| WO | 2009/087680 A2 | 7/2009 |

OTHER PUBLICATIONS

Hermann et al. Isolation and characterization of butanol-resistant mutants of Clostridium acetobutylicum. Appl Environ Microbiol. Nov. 1985;50(5):1238-43.*
International Search Report of PCT/IN2012/000536 dated Mar. 13, 2013, 3 pages.
Evans, P. J., Wang, H. Y. (1988). Enhancement of Butanol Formation by *Clostridium acetobutylicum* in the Presence of Decanol-Oleyl Alcohol Mixed Extractants. Applied and Environmental Microbiology, 54(7): 1662-1667.
Mutschlechner, O., Swoboda, H., Gapes, J. R. (2000). Continuous Two-Stage ABE-Fermentation using *Clostridium beijerinckii* NRRL B592 Operating with a Growth Rate in the First Stage Vessel Close to its Maximal Value. J. Mol. Microbiol. Biotechnol. 2(1): 101-105.
Jones D. T., Woods, D. R. (1986). Acetone-Butanol Fermentation Revisited. Microbiological Reviews. 50(4): 484-524.
Ghose, T. K., Kostick, J.A. (1970). A Model for Continuous Enzymatic Saccharification of Cellulose with Simultaneous Removal of Glucose Syrup. Biotechnology and Bioengineering, 12: 924-946.
Baer, S.H., Blaschek, H.P., Smith, T.L. (1987). Effect of butanol challenge and temperature on lipid composition and membrane fluidity of butanol-tolerant *Clostridium acetobutylicum*. Applied and Environmental Microbiology. 53(12): 2854-2861.
Ezeji, T.C., Qureshi, N., Blaschek, H. P. (2007). Bioproduction of butanol from biomass: from genes to bioreactors. Current Opinion in Biotechnology. 18: 220-227.
Herrera, S. (2004). Industrial biotechnology—a chance at redemption. Nature Biotechnology. 22 (6): 671-678.
King, A. J., He, W., Cuevas, J.A., Freudenberger, M., Ramiaramanana, D., Graham, I. A. (2009). Potential of *Jatropha curcas* as a source of renewable oil and animal feed. Journal of Experimental Botany. 60(10): 2897-2905.
Lazaroaie, M. M. (2009). Mechanisms Involved in Organic Solvent Resistance in Gram-Negative Bacteria. International Journal of Biological, Biomolecular, Agricultural, Food and Biotechnological Engineering. 3(6): 309-319.
Lee, P. C., Lee, W. G., Kwon, S., Lee, S. Y., Chang, H. N. (2000). Batch and continuous cultivation of *Anaerobiospirillum succiniciproducens* for the production of succinic acid from whey. Appl. Microbiol. Biotechnol. 54: 23-27.

(Continued)

*Primary Examiner* — Yong Pak
(74) *Attorney, Agent, or Firm* — Collard & Roe, P.C.

(57) ABSTRACT

The production of butanol by the mutant *Clostridium acetobutylicum* MTCC 5587 using an acid pretreated biomass such as *jatropha* seed cake, *pongamia* seed cake and banana stems as renewable feedstock. Chemical mutagenesis was carried out for improvement of the strain for better butanol tolerance and production. This leads to a high yield of butanol obtained in single batch fermentation using acid pretreated *jatropha* seed cake.

18 Claims, 5 Drawing Sheets

(56) References Cited

OTHER PUBLICATIONS

Liang, Y., Siddaramu, T., Yesuf, J., Sarkany, N. (2010). Fermentable sugar release from Jatropha seed cakes following lime pretreatment and enzymatic hydrolysis. Bioresource Technology. 101 : 6417-6424.

Li, J., Zhao, J. B., Zhao, M., Yang, Y.L., Jiang, W.H., Yang, S. (2010). Screening and characterization of butanol-tolerant micro-organisms . Letters in Applied Microbiology. 50: 373-379.

Long, S., Long, D. T., Woods, D. R. (1984). Initiation of solvent production, clostridial stage and endospore formation in *Clostridium acetobutylicum* P262. Applied Microbiology and Biotechnology. 20: 256-261.

Nishino, K., Yamaguchi, A. (2004). Role of histone-like protein H-NS in multidrug resistance of *Escherichia coli*. Journal of Bacteriology. 186(5): 1423-1429.

Papoutsakis, E.T (2008). Engineering solventogenic clostridia. Current Opnion in Biotechnology. 19: 420-429.

Parekh, M., Formanek, J., Blaschek, H.P. (1998). Development of a cost-effective glucose-corn steep medium for production of butanol by *Clostridium beijerinckii*. Journal of Industrial Microbiology & Biotechnology. 21: 187-191.

Pfromm, H. P., Amanor-Boadu, V., Nelson, R., Vadlani, R, Madl, P., (2010). Bio-butanol vs. bio-ethanol: A technical and economic assessment for corn and switchgrass fermented by yeast or *Clostridium acetobutylicum*. Biomass and Bioenergy. 34: 515-524.

Qureshi, N., Saha, C. B., Hector, R. E., Dien, B., Hughes, S., Liu, S., Iten, L., Bowman, M. J., Sarath, G., Cotta, M. A. (2010). Production of butanol (a biofuel) from agricultural residues: Part II—Use of corn stover and switchgrass hydrolysates. Biomass and Bioenergy. 34: 566-571.

Samuelov, N. S., Lamed, R., Lowe, S., Zeikus, J. G. (1991). Influence of $CO_2$—$HCO_3$ levels and pH on growth, succinate production, and enzyme activities of *Anaerobiospirillum succiniciproducens*. Applied and Environmental Microbiology 57(10): 3013-3019.

Sharma, Y., Singh B., Korstad, J. (2010). High yield and conversion of biodiesel from a nonedible feedstock (*Pongamia pinnata*). Journal of Agricultural and Food Chemistry. 58(1): 242-247.

Sikkema, J., de Bont, J.A.M. , Poolman, B. (1995). Mechanisms of membrane toxicity of hydrocarbons. Microbiological Review. 59(2): 201-222.

Vollherbst-Schneck, K., Sands, J.A., Montenecourt, B. S. (1984) Effect of Butanol on Lipid Composition and Fluidity of *Clostridium acetobutylicum* ATCC 824. Applied and Environmental Microbiology, 47(1): 193-194.

Tomas, C.A., Welker, N. E., Papoutsakis, E. T. (2003). Overexpression of groESL in *Clostridium acetobutylicum* results in increased solvent production and tolerance, prolonged metabolism, and changes in the cell's transcriptional program. Applied and Environmental Microbiology. 69(8): 4951-4965.

Tomas, C. A., Beamish, J., Papoutsakis, E.T. (2004). Transcriptional analysis of butanol stress and tolerance in *Clostridium acetobutylicum*. Journal of Bacteriology. 186(7): 2006-2018.

Zainol, N., Abdul-Rahman, R. (2008). Abstract of Anaerobic cellulose recovery from banana stem waste. Proceedings International Conference on Environmental Research and Technology.

Jesse, T.W., Ezeji, T.C., Quershi, N. Blaschek, H.P. (2002) Production of butanol from starch-based waste packing peanuts and agricultural waste. 29: 117-123.

\* cited by examiner

Fig. 1. Tolerance and growth of the mutant strain in presence of different concentrations of butanol.

Fig. 2. Comparison of the fatty acid profile of wild type (A) and mutant strain (B)

Fig. 3. Rhodamine G accumulation in wild type and solvent tolerant mutant of C. *acetobutylicum*

Fig. 4. HPLC chromatograms of standard butanol (A) and fermented broth (B).

Fig. 5. Profile of scale up of butanol production from jatropha seed cake hydrolysate

BUTANOL FERMENTATION USING ACID PRETREATED BIOMASS

CROSS REFERENCE TO RELATED APPLICATIONS

This application is the National Stage of PCT/IN2012/000536 filed on Aug. 1, 2012, which claims priority under 35 U.S.C. §119 of Indian Application No. 2181/MUM/2011 filed on Aug. 1, 2011, the disclosures of which are incorporated by reference.

FIELD OF THE INVENTION

The present invention relates to a efficient process for the production of high yield of butanol using a mutant strain of *Clostridium acetobutylicum* ATCC 4259 from biomass with enhanced butanol tolerance.

BACKGROUND OF THE INVENTION

Petroleum-derived fuels have served the mankind for ages. However, the recent awakening to the realization of dismal scenario of fossil fuel availability, perils of petroleum resource exhaustion, and stringent environmental legislation governing worldwide, has led to search for alternative energy sources (Herrera et al., 2004; Li et al 2010). Therefore, several alternative fuels are being investigated, which can either completely replace the petroleum derived fuels (gasoline and diesel) or can be blended with petroleum fuels to certain proportions, without requiring specially adopted engines in vehicles.

Amongst the other alternative fuels, Butanol was found to be of the best choice as it is superior replacement for gasoline, meeting the societal needs. Biobutanol is unequivocally a better fuel replacement for gasoline and is preferred in other industries for safety reasons. Being renewable, butanol helps in curbing the now so-called notorious "carbon" and other harmful emissions in the form of hydrocarbons; particulate matter; benzene, toluene, ethylbenzene, xylene (BTEX); and other undesirable elements (Sharma et al., 2010).

Butanol or butyl alcohol (sometimes also called biobutanol when produced biologically), is a primary alcohol with a 4 carbon structure and the molecular formula of $C_4H_{10}O$. It is primarily used as a solvent, as an intermediate in chemical synthesis, and as a fuel. Today, there is a paramount interest in producing fuels like butanol and ethanol using microorganisms by fermentation focusing on the environmental aspects and renewable nature of this mode of production. Butanol is a superior fuel and has more calorific value than ethanol (Qureshi and Blascher, 2000). Butanol has higher energy content (110,000 Btu's per gallon for butanol vs. 84,000 Btu per gallon for ethanol). It is six times less "evaporative" than ethanol and 13.5 times less evaporative than gasoline, can be shipped through existing fuel pipelines where ethanol must be transported via rail, barge or truck (Jones and 'Woods, 1986).

Butanol is an important industrial solvent and potentially a better fuel extender than ethanol. Current butanol prices as a chemical are at $3.75 per gallon, with a worldwide market of 370 million gallons per year. The market demand is expected to increase dramatically if green butanol can be produced economically from low cost biomass. In addition to its usage as fuel, butanol can be used as a solvent for a wide variety of chemical and textile processes, in organic synthesis and as a chemical intermediate. It is also used as paint thinner and a solvent in other coating applications where it is used as a relatively slow evaporating latent solvent in lacquers and ambient-cured enamels. It finds other uses such as a component of hydraulic and brake fluids (Mutschlechner et al, 2000)/It is also used as a base for perfumes, but on its own has a highly alcoholic aroma.

Since the 1950s, most butanol in the United States is produced commercially from fossil fuels. The most common process starts with propene, which is run through an hydroformylation reaction to form butanal, which is then reduced with hydrogen to butanol. Butanol is produced by fermentation, from corn, grass, leaves, agricultural waste and other biomass.

Production of industrial butanol and acetone via fermentation, using *Clostridium acetobutylicum*, started in 1916. Chime Wizemann, a student of Louis Pasteur, isolated the microbe that made acetone. Up until the 1920s, acetone was the product sought, but for every pound of acetone fermented, two pounds of butanol were formed. A growing automotive paint industry turned the market around, and by 1927 butanol was primary and acetone became the byproduct.

The production of butanol by fermentation declined from the 1940s through the 1950s, mainly because the price of petrochemicals dropped below that of starch and sugar substrates such as corn and molasses. The labor intensive batch fermentation system's overhead combined with the low yields contributed to the situation. Fermentation-derived acetone and butanol production ceased in the late 1950s.

Acetone butanol ethanol (ABE) fermentation by *Clostridium acetobutylicum* is one of the oldest known industrial fermentations. It was ranked second only to ethanol fermentation by yeast in its scale of production, and is one of the largest biotechnological processes ever known. The actual fermentation, however, has been quite complicated and difficult to control. ABE fermentation has declined continuously since the 1950s, and almost all butanol is now produced via petrochemical routes. In a typical ABE fermentation, butyric, propionic, lactic and acetic acids are first produced by *C. acetobutylicum*, the culture pH drops and undergoes a metabolic "butterfly" shift, and butanol, acetone, isopropanol and ethanol are formed. In conventional ABE fermentations, the butanol yield from glucose is low, typically around 15 percent and rarely exceeding 25 percent.

The key problem associated with butanol production is butanol toxicity/inhibition of the fermenting microorganism, resulting in low butanol titer in the fermentation broth. (Ezeji et al, 2007). The production of butanol was limited by severe product inhibition. Butanol at a concentration of 1% can significantly inhibit cell growth and the fermentation process. Consequently, butanol concentration in conventional ABE fermentations is usually lower than 1.3 percent. Butanol is highly toxic to biological systems at quite low concentrations of 2% (Jones and Wood, 1986). This toxicity may be because butanol localizes in the plasma membrane and disrupts a number of physiological processes including membrane permeability, solute transport, and maintenance of proton motive force, conformation and activity of intrinsic membrane proteins. Efforts are being made to improve the butanol tolerance level in different species of *Clostridia* with varying degree of success (Evan and Wang, 1988). Recent interest in the production of butanol has led to re-examination of ABE fermentation, including strategies for reducing or eliminating butanol toxicity to the culture.

In the past 20+ years, there have been numerous engineering attempts to improve butanol production in ABE fermentation, including cell recycling and cell immobilization to increase cell density and reactor productivity and using extractive fermentation to minimize product inhibition.

Despite many efforts, the best results ever obtained for ABE fermentations to date are still less. Optimizing the ABE fermentation process has long been a goal of the industry.

Butanol is currently produced worldwide at over 1.4 billion gal/year by chemical route. The market demand is expected to increase dramatically if butanol can be produced economically from low-cost biomass. Therefore, development of processes to produce biobutanol using renewable energy sources such as lignocellulosic crops is gaining impetus (Qureshi et al., 2010).

U.S. Pat. No. 4,521,516 provides a novel asporogenic strain of *C. acetobutylicum* produced by growing a spore-forming strain in a continuous culturing reactor. Culturing is conducted at a dilution rate which prevents accumulation of butanol and acetone in the medium. Culturing at this dilution rate is continued until the asporogenic strain is obtained.

U.S. Pat. No. 5,192,673 provide a biologically pure asporogenic mutant of *C. acetobutylicum* is produced by growing sporugenic *C. acetobutylicum* ATCC 4259 and treating the parent strain with ethane methane sulfonate. The mutant which has been designated *C. acetobutylicum* ATCC 55025 is useful in an improved ABE fermentation process, and produces high concentrations of butanol and total solvents. However the fermentation herein includes three stage continous fermentation hereby making the process expensive and time consuming.

U.S. Pat. No. 6,358,717 provide a method of producing high levels of butanol using a fermentation process that employs a mutant strain of *Clostridium beijerinckii*. The mutant is a hyperamylolytic strain that is able to produce high titres of butanol in a glucose/starch rich medium. However there is no claim on the solvent tolerance of the strain.

U.S. Pat. No. 4,757,010 and European patent application EP 00111683 provides an improved strain of *Clostridium* for increased tolerance to butanol. JP03058782 provides *Clostridium pasteurianum* CA 101 stock (FERM P-10817) as a mutant of genus *Clostridium bacterium* having analog resistance to fermented intermediate of butanol and butanol producibility. U.S. Pat. No. 4,539,293 demonstrates the use of co-culture of microorganisms of the *Clostridium* genus, one favors the production of butyric acid and the other supports the formation of butanol. Japanese patent application J P 63157989 provides production of butanol by culturing a different strain *Clostridium pasteurianum* var. 1-53 (FERM P-9074) in a liquid medium containing a carbon source, a nitrogen source and other inorganic salts at 28-33 deg. C. under slightly acidic pH condition in anaerobic state for 2-4 days.

U.S. Pat. No. 4,777,135 describes a method of producing butanol by fermentation which comprises culturing under anaerobic conditions a butanol-producing microorganisms in a culture medium containing fluorocarbons. This process is not feasible on a commercial scale as the fluorocarbons are environmentally not safe U.S. Pat. No. 4,605,620 provides a process for butanol by using a medium containing carbohydrate and phosphate, wherein the experiments were performed with a total phosphate content of 1.0-0.4 mmoles. This process poses a restriction wherein the phosphate limiting medium is required.

U.S. Pat. No. 4,560,658 provides a process for the production of butanol by fermentation of carbon containing compounds with *C. acetobutylicum* wherein the fermentation is conducted in an aqueous medium containing a sufficient concentration of dissolved carbon monoxide. However the use of carbon monoxide makes the process environmentally unsound.

U.S. Pat. No. 4,520,104 provides a process for the continuous production of butanol by fermentation of carbohydrates with *C. acetobutylicum*. This process combines continuous inoculum production at a high dilution rate and cycling the fermentation broth through material which adsorbs butanol whereby a vigorous cell population is maintained in the fermentation reactor for extended periods of time. The process is devised to remove the butanol produced in the broth so as to prevent its toxicity on the cells Japanese patent JP 62278989 provides a fermentation process for the production of acetone and butanol, by keeping a butanol-producing strain in resting state, adding a carbon source to the cell to effect the production of acetone and butanol in a short time, recovering and concentrating the butanol-producing strain, subjecting to the heat shock and adding to a fermentation tank Heat shock is required in the process.—to activate the spores of *Clostridium* and is pretty routine.

Japanese patent application provides an anaerobic cellulolytic germ, e.g. *Clostridium cellobioparum* ATCC 15832 or *Ruminococcus albus* ATCC2721 1, and *Clostridium saccharoperbutylacetonicum* are inoculated into a culture medium containing a material containing cellulose, e.g. wood, waste paper or pulp, as a main carbon source, and cultivated at 25-45° C. and 4-9 pH under anaerobic conditions for about 2-20 days to collect the aimed compound, containing oxygen, and consisting essentially of butanol from the resultant culture. This process is time consuming and takes about 20 days for completion, hence not feasible on a large scale.

Japanese patent 63269988 discloses butanol fermentation wherein yeast is subjected to autodigestion in a fermentation tank and proliferated prior to the inoculation of butanol-producing strain. The space in the fermentation tank becomes anaerobic and the temperature increases by the proliferation of yeast to perform butanol fermentation. An inefficient autodigestion would lead to contamination of the broth by the yeast US20050233031 provides a process for producing butanol which includes treating plant derived material to provide an aqueous liquor containing sugars in a fermentation process to produce a fermentation product. The process involves several steps and therefore cumbersome and tedious.

Japanese Patent JP 200535328801 provides a method for producing butanol in which a culture solution is prepared by using a formulation of the food residue with the Japanese distilled spirit lees and water and butanol fermentation is carried out in the culture solution. The use of Japanese distilled spirit is limited to the production experiments performed in Japan.

French patent FR2550222 provides a two stage process wherein a first stage of seeding with *C. acetobutylicum* and a second stage of seeding with yeast which produces ethanol, the second stage being commenced when the pH of the fermentation medium of the first stage has reached a minimum value. The invention applies in particular to the production of butanol, acetone and ethanol from sugar beet and Jerusalem artichoke juices.

Indian patent application 2544/MUM/2007 provides a process for production of high yields of butanol by *Clostridium acetobutylicum* ATCC 10132. The process can be completed in a shorter span of time, using batch process through manipulation of various process parameters. The process can also be used for biomass based production of butanol. The process requires commercial media whereas in the present invention acid pretreated feedstock is utilised along with the mutant strain of *Clostridium acetobutylicum* resulting in higher yields of butanol with enhanced butanol tolerance.

The commonly employed feedstocks as reported in the literature for biobutanol synthesis are corn (*Zea mays*), banana stems (*Musa sapientum*), jatropha (*Jatropha curcas*), and karanja (*Pongamia pinnata*) (Liang et al., 2010, Pfromm et al., 2010). However, the use of food crops like corn, sugarcane, etc. will lead to the food v/s fuel situation. In order to avoid this situation, it becomes imperative to explore the potential non-edible feedstocks and their suitability for biobutanol synthesis.

Among the many feedstocks available for biobutanol production, *jatropha* and karanja have been found to be most suitable due to their favourable attributes such as hardy nature, short gestation time of about 3 years, productive life of 50-100 years, not browsed by animals, adaptability to varied agro-climatic conditions and soil type, drought resistance and non competing with food crops for land and water sources.

The present invention provides the use of lignocellulosic biomass like *jatropha* seed cake and *pongamia* seed cake which is acid pretreated to disarray the cellulosic structure for extracting maximum reducing sugar. The hydrolysed sugar was used along with AnS medium components for biobutanol production.

The present invention also provides the use of the cellulose rich biomass i.e. banana stems which is acid pretreated to that release sugar which after hydrolysis produces biobutanol.

Although, there are reports where microbes have been exploited for the production of butanol by fermentation, there arises the need for an economically viable biosynthetic process for butanol production yet to be developed (Jesse et al, 2002).

The drawback associated with butanol production is butanol toxicity/inhibition of the fermenting microorganism, resulting in low butanol titer in the fermentation broth. Economic analysis has suggested that if butanol titers could be raised from 12 to 19 g/L, the separation cost could be cut down to half (Papoutsakis, 2008). Normally, the final titer of butanol in fermentation does not surpass 13 g/L because of feedback inhibition (Jones and Wood, 1986). Beyond this level, butanol is toxic to the bacterial cell and disrupts the membrane fluidity and function (Volherbst-Schneck et al., 1984).

In order to combat the effect of butanol toxicity, tolerant strains over express certain heat shock proteins (HSPs) like GroEL (Thomas et al., 2003, 2004) and alters its lipid composition by having more saturated fatty acids. This response known as 'homeoviscous adaptation', is believed to offset the physical changes caused by the environment and permits the cell to maintain its membrane at proper viscosity and surface ionic milieu for optimal cellular function (Baer et al., 1987).

According to the literature (Nishino and Yamaguchi, 2004), rhodamine 6G is P-glycoproteins substrate, mediates the energy-dependent efflux of certain toxic compounds from the bacterial cells. The existence of solvent efflux pumps in the cells can therefore be confirmed by rhodamine 6G accumulation in bacterial cells (Lazaroaie, 2009). The inventors of the present invention have used the above literature reference for assaying the solvent tolerant mutant strain and the wild type strain of *C. acetobutylicum* used for production of butanol.

Techniques such as gas stripping have been practiced to overcome the inhibitory effect of butanol produced during fermentation run (Ezeji et al., 2007). However, the process is plagued with inconsistent results and high energy expenditure. In the present invention, the inhibitory effect of butanol was overcome by improving the butanol tolerance of the microbe using chemical mutagenesis.

To combat the drawbacks of earlier inventions as cited in the prior art there arises the need for a process which yields enhanced production of butanol. In light of this the present invention has been focused on developing an ideal culture condition for the mutant strain of *Clostridium* which will result in enhanced butanol tolerance and subsequently the increase in yields of butanol.

OBJECT OF THE INVENTION

It is the object of the present invention to provide an efficient process for the production of high yield of butanol from pretreated biomass using a solvent tolerant mutant of *Clostridium acetobutylicum*.

It is the object of the present invention to provide optimal fermentation conditions for enhanced production of butanol, using *Clostridium acetobutylicum* mutant.

It is the object of the present invention to employ chemical mutagenesis for improvisation of the strain for better butanol tolerance and production.

It is the object of the present invention to provide a process with optimal fermentation conditions, which will result in increased butanol tolerance of the microorganism.

It is the object of the present invention to provide a culture condition for high yields of butanol fermentation.

It is the object of the present invention to provide a process for increased yields of butanol in a single batch fermentation conditions.

It is the object of the present invention to provide a process for biobutanol using various acid pretreated biomass.

It is the object of the present invention to provide a cost effective and industrially scalable process for butanol.

SUMMARY OF THE INVENTION

In the first embodiment the present invention relates to an efficient process for the production of high yield of butanol using a solvent tolerant mutant of *Clostridium acetobutylicum* from biomass. The present invention in particular aims at providing optimal culture conditions that would result in increased butanol tolerance of the mutant strain of the microorganism. The present invention further aims at providing a cost effective and industrially scalable process for the production of butanol.

The. second embodiment relates to the production of high yields of butanol (upto 19 g/L) in a single batch process, without stripping the butanol produced. Here in the process doesn't involve any fed-batch step which would involve extra step of addition of nutrients nor any solvent-stripping is required for reaching this high yield. Unlike many reported processes in the public domain which employ continuous mode of fermentation thereby increasing the chances of contamination, the present invention includes a process that can be completed in a single batch mode. Careful optimization of the medium, acclimatisation and chemical mutagenesis for improvisation has resulted in a mutant strain that is capable of producing and tolerating such high yields of butanol in the broth. Thus, all these parameters make the process of the present invention more cost-effective. Further the inventors have also been able to successfully demonstrate the process at 15 L scale.

The third embodiment of the present invention provides a process for increased butanol tolerance by chemical mutagenesis of the strain. In one preferred aspect the present invention provides tolerance to about 3.5% butanol concentration under optimized medium; conditions directed to a process for providing the increased yield of butanol as provided in this invention. The most probable reason for its high tolerance to butanol may be that the process optimization has resulted in the final set of physio-chemical, conditions under which the above mentioned limitations are alleviated. For example the redox potential, osmolarity, electron flow may have been altered under the optimized conditions. Certain set of enzymes required for butanol tolerance and production may have been activated or induced under the optimized conditions. The culture may have adapted during the course of the optimization process to high butanol level.

Fourth embodiment covers the aspect of the present invention to provide a process for evaluation of the biobutanol using various biomass. In one preferred aspect the seed cake from *jatropha* and *pongamia* and banana stems were used. The yield of biobutanol using the seed cake and stems pretreated using acid hydrolysis was also studied.

Last embodiment relates to the present invention providing a process which can be scaled up on a large scale.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

Figure 1:
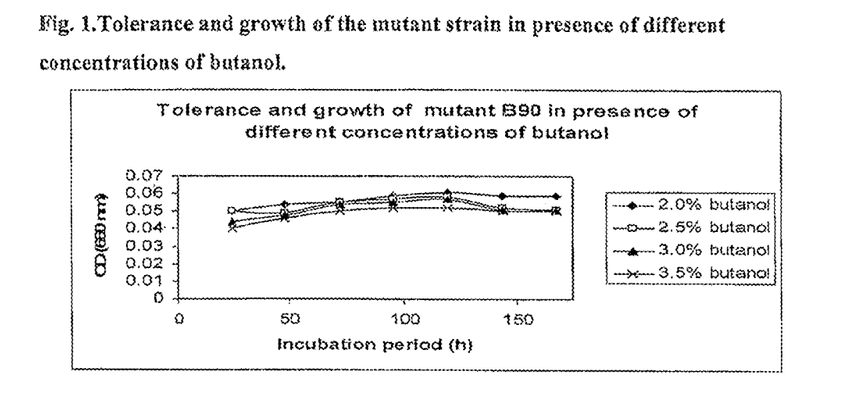
FIG. 1. Tolerance and growth of the mutant strain, designated as B90, in presence of different concentrations of butanol.

It was observed that the wild type strain *C. acetobutylicum* ATCC 4259 could tolerate up to 1.5% butanol in the medium beyond which there was cessation of growth whereas, the mutant strain *C. acetobutylicum* MTCC 5587 (B90) could tolerate up to 3.5% (v/v) butanol in the AT medium. The growth at these levels of butanol was extremely slow and feeble due to the toxicity of the solvent. At higher concentrations i.e. 3.8% and 4%, there was no growth.

Figure 2:
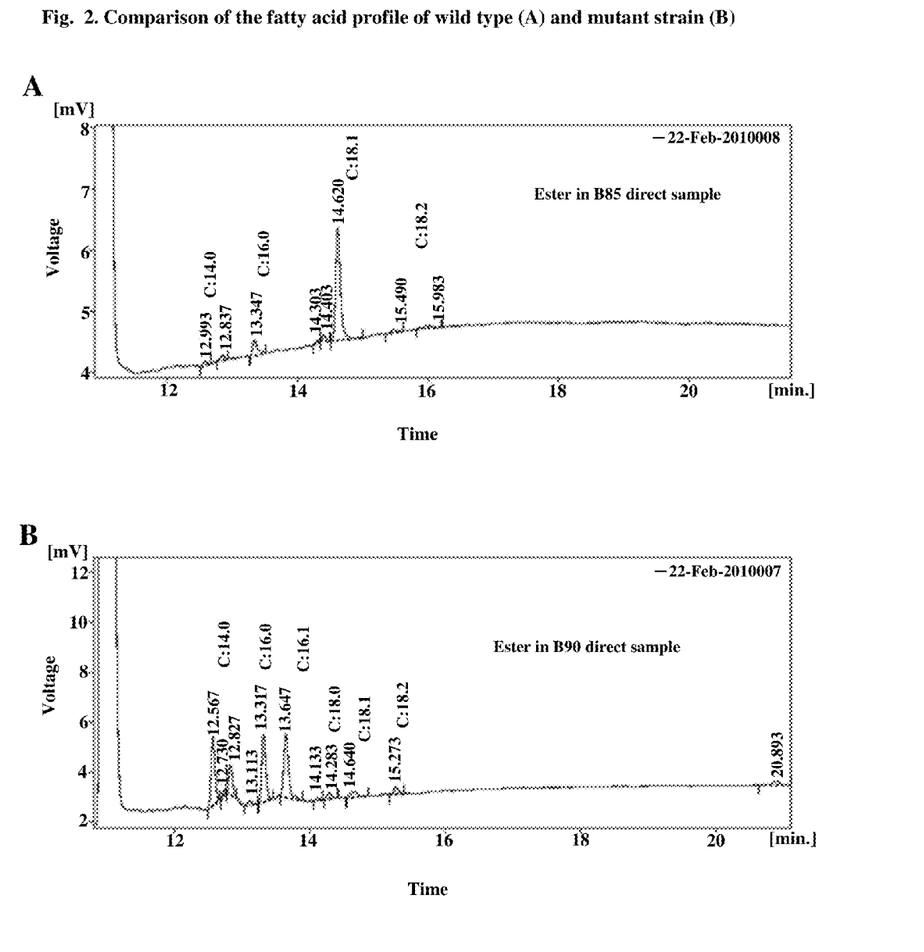
FIG. 2 Comparison of the fatty acid profile of wild type (A) and mutant strain (B)

The total lipids of the wild type and the solvent tolerant mutant strain were extracted and analysed by GC. The lipid composition of the mutant, *C. acetobutylicum* MTCC 5587 was found to be altered as compared to the wild type strain. The GC profile (FIG. 2B) showed the presence of the saturated fatty acids, viz. myristic (C14:0) and palmitic acid (C16:0) comprising about 50% of total fatty acids in the solvent tolerant strain with only traces of unsaturated fatty acids. Whereas, in the wild type, the unsaturated fatty acid, oleic acid (C18:1) was abundant constituting about 75% of total fatty acids and the saturated fatty acids were in significantly lower quantities (11% of C16:0) (FIG. 2A).

Figure 3:
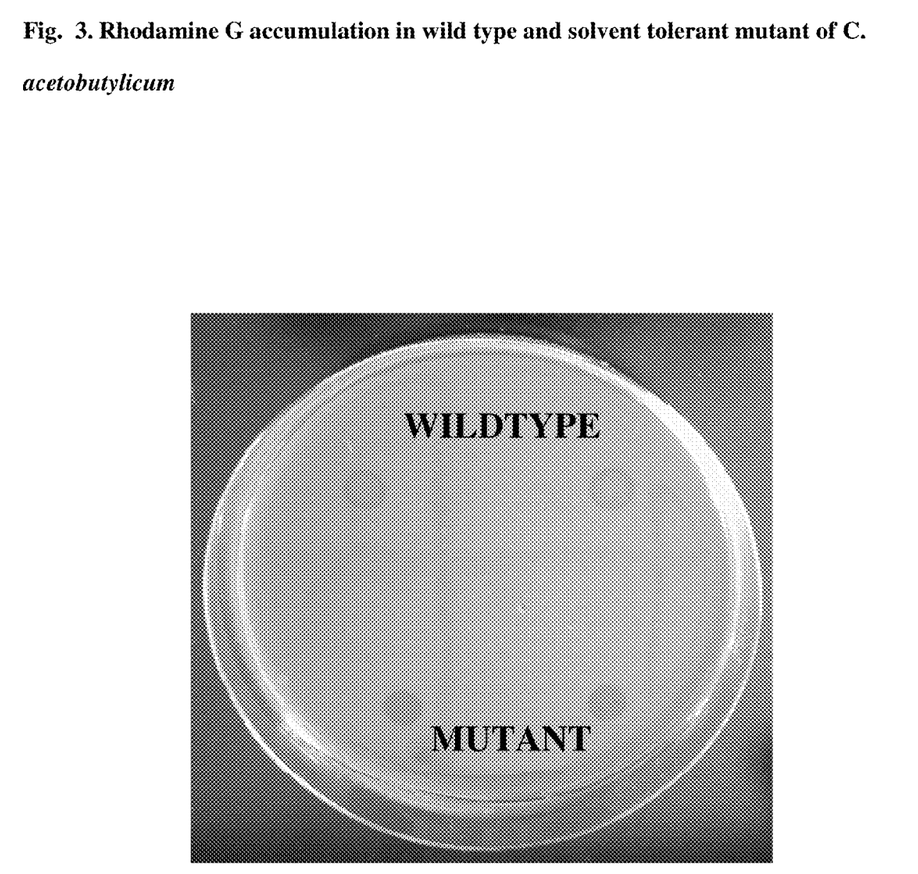
FIG. 3 Rhodamine G accumulation in wild type (A) and solvent tolerant mutant of *C acetobutylicum* (B).

While studying it was seeing that after 24 h incubation on a plate containing the toxic dye Rhodamine 6G, the mutant strain was found to have high accumulation of rhodamine 6G intracellularly appearing as pink colony (FIG. 3). Whereas the colony of the wild type strain was a faint pink with comparatively lower dye accumulation. This indicates the existence of tolerance mechanism to toxic compounds such as butanol in the mutant strain.

The process was further scaled up to 15 L level in a 20 L bioreactor using 7% (w/v) *jatropha* seed cake and 2% glucose. A butanol titre of 18.6 g/L was achieved in 72 h FIG. 5 Profile of scale up of butanol production from *jatropha* seed cake hydrolysate.

Figure 5:
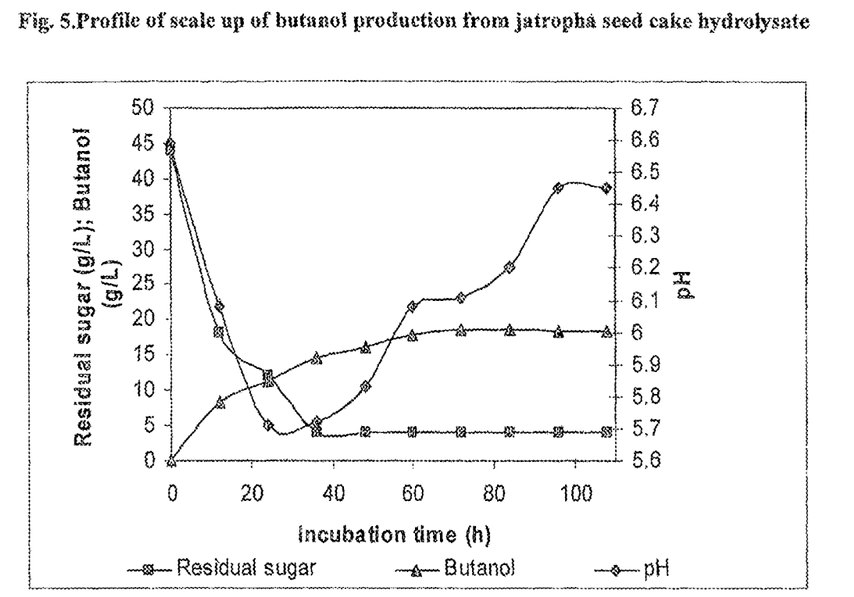

The initial sugar was 44 g/L and the final sugar was 4 g/L (FIG. 5). The typical butterfly shift could be observed when the acidogenic phase declined and solventogenic phase commenced.

DETAILED DESCRIPTION OF THE INVENTION

Definitions

The term Butanol or biobutanol as used herein refers to n-butanol.

The term butanol tolerance as used herein refers to the ability of the bacterium to survive and grow in the presence of 2.5-3.5% butanol in the medium The term *Clostridium acetobutylicum* refers to the bacteria that has the ability to produce butanol along with acetone and ethanol in a anaerobic fermentation The term yield as used herein refers to amount of butanol produced in the fermentation broth in g/L.

The term mutant strain relates to *C. acetobutylicum* MTCC 5587. This mutant strain has been deposited in Microbial Type Culture Collection, Chandigarh, India under the Budapest treaty and designated the number MTCC 5587.

One of the important factors that affect both growth and growth-associated production of molecules is pH, in the present invention butanol production was examined at different pH. The optimal pH for butanol production by *Clostridium acetobutylicum* mutant in the present invention was 6.5. This is in accordance to the findings of Robson and Jones (1982), who reported that *C. acetobutylicum* P262 showed good levels of solvent production within the pH range of 5.0-6.5. Similarly, Bielbl (1999) reported that *Clostridium beijerinkii* NCIMB 8052 showed much better growth and solvent production at pH 5.5 than at pH 5.0 or below.

Another important factor that affects both growth and growth-associated production of molecules is temperature. In the present invention it was found that at optimal growth temperatures higher yield of butanol was produced for mutant MTCC 5587. This is in contrast to the earlier findings of McCutchan and Hickey (1954) who reported a decrease (upto 23%) in the solvent production by *Clostridium* sp. at 37° C. as against the fairly constant yields of 31% at 30 and 33° C.

It is well established that amongst the nutritional parameters, carbon source is one of the very important factors that is responsible for cell growth and biomolecule production (Samulov et al, 1991). In the present invention, the primary carbon source used was the sugar obtained after the hydrolysis of the biomass. However, to further enhance the cell growth and the production of butanol, glucose at different concentration (0-2%) was added to the hydrolysate. Results showed that the addition of glucose (2%) to the hydrolysate of acid pretreated *jatropha* seed cake (7%), supported butanol production up to 14.3 g/L in 120 h in 125 ml anaerobic vials. However, when no glucose was added, very low titre of butanol (4.2 g/L) was obtained. These results are in agreement with the findings of Parekh et al. (1998) who reported that corn steep water (CSW) medium alone was not a suitable substrate, whereas addition of glucose (6%) supported growth and butanol production. The effect of the nutrition limitation on the onset and maintenance of solvent production has been investigated by a several other workers as well. For example Long et al. (1984) reported that in the batch fermentation using *Clostridium acetobutylicum* P262, only acids were produced when the concentration of the carbon sources was limited. Besides, *jatropha* seed cake is known to be toxic due to presence of phorbol esters. Therefore, *jatropha* seed cake hydrolysate alone may not be conducive for the growth of the organism and butanol production.

As discussed earlier, butanol toxicity also is an important factor that affects production of butanol, this butanol toxicity is due to its localization in the plasma membrane resulting in disruption of a number of physiological processes including membrane permeability, solute transport, maintenance of proton motive force, conformation and activity of intrinsic membrane proteins (Sikkema et al., 1995). Solvent tolerant bacteria evade these reactions by cellular adaptations including altered membrane lipid composition, efflux system that actively decreases the solvent concentration inside the cell, degradation of solvents or over-expressing stress proteins such as heat shock proteins (HSPs) (Tomas et al, 2003, 2004).

One of the factors that have played a pivotal role in the present invention is achieving high titre of butanol by a single step process without resorting to any solvent stripping or dilution of the broth is the solvent tolerating ability of the mutant strain. To investigate the mechanism behind the tolerance, fatty acid composition of the total lipids was determined. A high proportion of saturated fatty acids C14:0 and C16:0 in mutant as compared to C18:1 in wild type is indicative of stimuli-driven alteration of lipid composition for survival.

Baer et al. (1987), reported that by synthesizing an increased amount of saturated fatty acids, mutant SA-1 of *Clostridium acetobutylicum* ATCC 824 developed a mechanism for combating the butanol stress.

Another finding was the ability of the mutant strain to accumulate increased amount of rhodamine 6G as compared to the wild type. This indicated the existence of a tolerance mechanism to toxic compounds viz. n-butanol which is in concurrence with Lazaroaie's (2009) report on the mechanism involved in organic solvent resistance in gram negative bacteria.

The mutant *Clostridium* strain used in the present invention has shown tolerance to 3.5% butanol. The most probable reason for its high tolerance to butanol may be that the chemical mutagenesis induced genetic alteration of the *Clostridium* strain and process optimization which resulted in the final set of physio-chemical conditions thereby overcoming the drawbacks of the processes cited in the public domain. For example, while the wild type strain barely produced any butanol, the mutant produced 4-5 g/L of butanol in a nutrient rich complex medium under unoptimised conditions. Subsequently, after optimization in a medium containing *jatropha* seed cake as depicted in Table 1, the mutant produced 14.3 g/L of butanol; a 3-fold increase.

Further studies on utilization of various biomass for butanol production using the conditions described above was performed. In particular, the biomass studied was *jatropha* seed cake, *pongamia* seed cake and banana stem. All the three types of biomass were subjected to acid hydrolysis and the total reducing sugar levels were estimated by dinitro salicylic acid method.

Deoiled *jatropha* seed cake and *pongamia* seed cake were dried and ground to fine powder. Different concentrations of the finely ground seed cake were treated with 1-3% HC1 or $H_2SO_4$ for 1-3 h at temperatures above 100° C. After acid treatment, the slurry was filtered using a muslin cloth and the filtrate was neutralized using NaOH. These acid pretreated filtrates were supplemented with AnS media. The pH of the medium was adjusted between 6-7 using conc. $H_2SO_4$ or NaOH. On using *jatropha* seed cake hydrolysate as the sole carbon source, the butanol titre was very poor with maximum of 4.2 g L in bottle containing 7% *jatropha* seed cake hydrolysate. Similarly, with 7% pongamic seed cake hydrolysate alone, a titre of 2.4 g/L was achieved. This indicated that for successful butanol fermentation to ensue, additional source of carbon needs to be supplemented. Addition of increasing amount of glucose led to corresponding increase in the titre (Table 1 and 2) for both *jatropha* and *pongamia* hydrolysates. A titre of 14.3 g/L of butanol was produced in the AnS medium having 7% *jatropha* hydrolysate having 2% glucose in 120 h (Table 1). Whereas, with 2% glucose and 7% *pongamia* hydrolysate, 8.7 g/L of butanol was produced (Table 2).

Experiments were also done on banana stems. The banana stems were cut into small pieces, sun dried and finely powdered. Different concentrations of the finely ground seed cake were treated with 1-3% HC1 or $H_2SO_4$ for 1-3 h at temperatures above 100° C. After acid treatment, the slurry was filtered using a muslin cloth and the filtrate was neutralized using NaOH. These acid pretreated filtrates were supplemented with AnS media. The pH of the medium was adjusted to between 6-7 using conc. $H_2SO_4$ or NaOH. Banana stem hydrolysate could support butanol production without additional carbon source supplement and a titre of 9.1 g/L was achieved at 10% hydrolysate concentration. However, fortification with 2% glucose along with the banana stem hydrolysate boosted the titre to 18.0 g/L of butanol (Table 3).

Feedstocks like *jatropha* seed cake and *pongamia* seed cake used in the present invention are rich in lignin content. *Jatropha* seed cake comprises of 29.1% lignin and 15.9% cellulose. Lignin is a complex polymer of phenyl propane units, which are cross-linked to each other by different chemical bonds. It is particularly difficult to biodegrade, and reduces the bioavailability of the other cell wall constituents. It is the most recalcitrant component of the plant cell wall; the higher the proportion of lignin, the lower the bioavailability of the substrate (Sjostrom, 1993).

On the other hand, banana stem consists of 63.9% cellulose and 12.3% lignin. Cellulose is a polysaccharide and is easily hydrolysable (Zainol and. Rehman, 2008). Therefore, efficient methods of pretreatments are required for the hydrolysis of the lignin component of these feedstocks.

In the present invention, we have carried out the acid hydrolysis of two lignocellulosic feedstocks such as *pongamia* and *jatropha* seed cake (at concentration 2%, 5%, 7%, 10%) for sugar hydrolysis along with the cellulosic biomass i.e. banana stem. Although maximum sugar was obtained in banana stem hydrolysate (at 10% concentration), detailed studies were performed only on *jatropha* seed cake hydrolysate due to its ready availability. Upon acid hydrolysis of different concentrations of *jatropha* seed cake, maximum amount (17.2 g/L) of reducing sugars could be obtained from 7% *jatropha* seed cake.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Organism and Growth Conditions

*Clostridium acetobutylicum* ATCC 4259 was grown in 125 ml bottles containing 50 ml of the Anaerobic Sugar (AnS)

medium having a composition (g/L): glucose, 20; peptone, 10; yeast extract, 5.0; $K_2HPO_4$, 3.0; NaCl, 1.0; $(NH_4)_2SO_4$, 1.0; $CaCl_2 2H_2O$, 0.2; $MgCl_2.6H_2O$, 0.2; and $Na_2CO_3$, 1.0 and pH was adjusted to 6.5.

The headspace was purged with $N_2$, and $Na_2S.9H_2O$ (0.02% (w/v)) was added to remove traces of dissolved oxygen (Samuelov et al, 1991; Lee et al, 2000). The glass bottles were sealed with butyl rubber caps and sterilized for 10 min at 121° C. The sterile medium was inoculated with 1-3% (v/v) seed culture and incubated at 37° C. for 132 h with intermittent gentle shaking.

EXAMPLE 2

Mutation Studies

Chemical mutagenesis was carried out using MNNG (1-methyl-3-nitro-1-nitrosoguanidine). Alternate thioglycolate (AT) media was inoculated with *C. acetobutylicum* ATCC 4259 from the stab culture. After 12 h growth at 37° C., the culture was harvested and centrifuged. The cell pellet was washed with 2 ml citrate buffer (pH 5.8) and 100 µl of MNNG (stock solution 100 mg/ml prepared in sterilized distilled water) was added to the cells, incubated at 30° C. for 70 min. The mutagenised cell mass was centrifuged and the supernatant discarded appropriately in biohazard containers. The cells were washed twice with AT broth and resuspended in 1 ml AT broth. The mutants were screened on AT agar plates containing 13 g/L butanol and incubated at 37° C. for 12-16 h.

EXAMPLE 3

Tolerance and Growth Profile of Butanol Tolerant Mutant

Mutants tolerant to 1.3% butanol were further screened for tolerance to higher concentration of butanol on AT agar medium containing (v/v) viz. 1.5%, 1.8%, 2.0%>, 2.5%) and 3.0%) butanol. One mutant growing on 3.0%> butanol containing AT agar medium plate was transferred to sealed 125 ml bottles containing 50 ml of AT medium having various amounts of butanol viz. (v/v) 2.0% o, 2.5%, 3.0% and 3.5%. The tolerance and growth profile of the mutant was monitored with respect to time.

The wild type strain *C. acetobutylicum* ATCC 4259 could tolerate up to 1.5% butanol in the medium beyond which there was cessation of growth. Whereas, the mutant strain *C. acetobutylicum* MTCC 5587 could tolerate up to 3.5% (v/v) butanol in the AT medium (FIG. 1). The growth at these levels of butanol was extremely slow and feeble due to the toxicity of the solvent. At higher concentrations i.e. 3.8% and 4%, there was no growth. The mutant has been deposited in Microbial Type Culture Collection, Chandigarh, India under the Budapest treaty and designated the number MTCC 5587.

EXAMPLE 4

Extraction of Lipids and Analysis

Total lipids were extracted from the cells as described in (Baer et al. 1987). The lipids were transesterified and FAMEs were analyzed by GC.

Total lipids of the wild type and the solvent tolerant mutant strain were extracted and analysed by GC. The lipid composition of the mutant, *C. acetobutylicum* MTCC 5587 was found to be altered as compared to the wild type strain. The GC profile (FIG. 2B) showed the presence of the saturated fatty acids, viz. myristic (C14:0) and palmitic acid (C16:0) comprising about 50% of total fatty acids in the solvent tolerant strain with only traces of unsaturated fatty acids. Whereas, in the wild type, the unsaturated fatty acid, oleic acid (C18:1) was abundant constituting about 75% of total fatty acids and the saturated fatty acids were in significantly lower quantities (11% of C16:0) (FIG. 2A).

EXAMPLE 5

Rhodamine 6G Accumulation

Cells of overnight culture of wild type and solvent-tolerant mutant *C. acetobutylicum* MTCC 5587 were spotted on AT agar with or without rhodamine 6G (100 µg/ml) and incubated at 37° C. in anaerobic chamber for 24 h. Accumulation of rhodamine 6G was monitored under UV light (Lazaroaie, 2009).

After 24 h incubation on a plate containing the toxic dye Rhodamine 6G, the mutant strain was found to have high accumulation of rhodamine 6G intracellular^ appearing as pink colony (FIG. 3). Whereas the colony of the wild type strain was faint pink with comparatively lower dye accumulation. This indicates the existence of tolerance mechanism to toxic compounds such as butanol in the mutant strain.

EXAMPLE 6

Process Optimization in Batch Fermentation

All optimization experiments were carried out in 50 ml AnS medium in 125 ml bottles. Different biomass viz. *jatropha* seed cake, banana stem and *pongamia* seed cake were subjected to acid hydrolysis as described below. All experiments were carried out at least thrice to ensure reproducibility.

EXAMPLE 7

Acid Hydrolysis of Different Feedstocks a. *Jatropha* Seed Cake and *Pongamia* Seed Cake Deoiled *jatropha* seed cake and *pongamia* seed cake were dried and ground to fine powder. Different concentrations of the finely ground seed cake were treated with 1-3% HCl or $H_2SO_4$ for 1-3 h at temperatures above 100° C. After acid treatment, the slurry was filtered using a muslin cloth and the filtrate was neutralized using NaOH. These acid pretreated filtrates were supplemented with AnS media. The pH of the medium was adjusted to 6.5 using conc. $H_2SO_4$ or NaOH.

b. Banana Stem

Banana stems were cut into small pieces, sun dried and finely powdered. Different concentrations of the finely ground banana stems were pretreated in the same way as described for the *jatropha* and *pongamia* seed cake.

All the three types of biomass were subjected to acid hydrolysis and the total reducing sugar levels were estimated by dinitro salicylic acid method. On using *jatropha* seed cake hydrolysate as the sole carbon source, the butanol titre was very poor with maximum of 4.2 g/L in bottle containing 7% *jatropha* seed cake hydrolysate. Similarly, with 7% *pongamia* seed cake hydrolysate alone, a titre of 2.4 g/L was achieved. This indicated that for successful butanol fermentation to ensue, additional source of carbon needs to be supplemented.

Addition of increasing amount of glucose led to corresponding increase in the titre (Table 1 and 2) for both *jatropha* and *pongamia* hydrolysates. A titre of 14.3 g/L of butanol was produced in the AnS medium having 7% *jatropha* hydrolysate having 2% glucose in 120 h (Table 1). Whereas, with 2% glucose and 7% *pongamia* hydrolysate, 8.7 g/L of butanol was produced (Table 2).

Banana stem hydrolysate could support butanol production without additional carbon source supplement and a titre^ of 9.1 g/L was achieved at 10% hydrolysate concentration. However, fortification with 2% glucose along with the banana stem hydrolysate boosted the titre to 18.0 g L of butanol (Table 3).

TABLE 1

Butanol production (g/L) at different ratio of glucose and *jatropha* seed cake hydrolysate

| | *Jatropha* seed cake concentration | | | |
|---|---|---|---|---|
| Glucose (%) | 2% | 5% | 7% | 10% |
| 0 | 2.0 | 3.2 | 4.2 | 3.9 |
| 0.5 | 5.2 | 6.4 | 8.9 | 8.1 |
| 1.0 | 7.1 | 8.9 | 10.8 | 10.2 |
| 1.5 | 8.5 | 10.1 | 12.2 | 12.0 |
| 2.0 | 9.1 | 12.8 | 14.3 | 13.8 |

TABLE 2

Butanol production (g/L) at different ratio of glucose and *Pongamia* cake hydrolysate

| | *Pongamia* seed cake concentration | | | |
|---|---|---|---|---|
| Glucose (%) | 2% | 5% | 7% | 10% |
| 0 | 1.4 | 1.9 | 2.4 | 2.0 |
| 0.5 | 3.3 | 4.0 | 4.9 | 4.3 |
| 1.0 | 4.9 | 5.8 | 6.2 | 6.0 |
| 1.5 | 6.0 | 7.0 | 8.0 | 8.1 |
| 2.0 | 6.6 | 7.9 | 8.7 | 8.4 |

TABLE 3

Butanol production (g/L) at different ratio of glucose and banana stems hydrolysate.

| | Banana stem concentration | | | |
|---|---|---|---|---|
| Glucose (%) | 2% | 5% | 7% | 10% |
| 0 | 2.7 | 3.4 | 5.3 | 9.1 |
| 0.5 | 5.5 | 8.9 | 9.6 | 10.7 |
| 1.0 | 7.8 | 11.6 | 12.4 | 13.8 |
| 1.5 | 10.3 | 12.2 | 15.8 | 17.8 |
| 2.0 | 11.6 | 13.7 | 16.9 | 18.0 |

EXAMPLE 8

Estimation of Butanol and Residual Sugar

The culture supernatant was analyzed for butanol by HPLC on PRP 300× column (Hamilton) with acetonitrile and 0.5 mM $H_2SO_4$ (1:9) as the mobile phase at a flow rate of 1.5 ml/min using RI detector. Butanol elutes at a retention time of 7.3 min. Residual sugar in the fermentation medium was estimated by dinitro salicylic acid method (Tasun and Ghen, 1970).

EXAMPLE 9

Validation of Production Process in 500 ml Anaerobic Bottles

Butanol production in the optimized medium was validated at 300 ml scale in a 500 ml bottle. The fermentation was carried out for 132 h and butanol production was estimated. Validation of the process at 300 ml scale in 500 ml bottles resulted in 14.8 g/L of butanol in 96 h in AnS medium having 7% *jatropha* seed cake hydrolysate and 2% glucose.

EXAMPLE 10

Scale Up of the Process to 15 L

Under the optimized conditions, scale up of the butanol production was carried out in a 20 L bioreactor with a working volume of 15 L. Fermentation was carried out for 108 h at 37° C. with constant agitation at 150 rpm. The initial pH of the medium was set at 6.5. Foaming was controlled by adding silicon antifoam agent. Anaerobiosis was maintained throughout the experiment by flushing $N_2$ gas constantly into the medium at a rate of 0.5 L/min through a sterile filter. Samples were collected at regular time interval of 12 h and processed for estimation of residual sugar, pH and butanol concentration in the fermentation broth.

Figure 4:
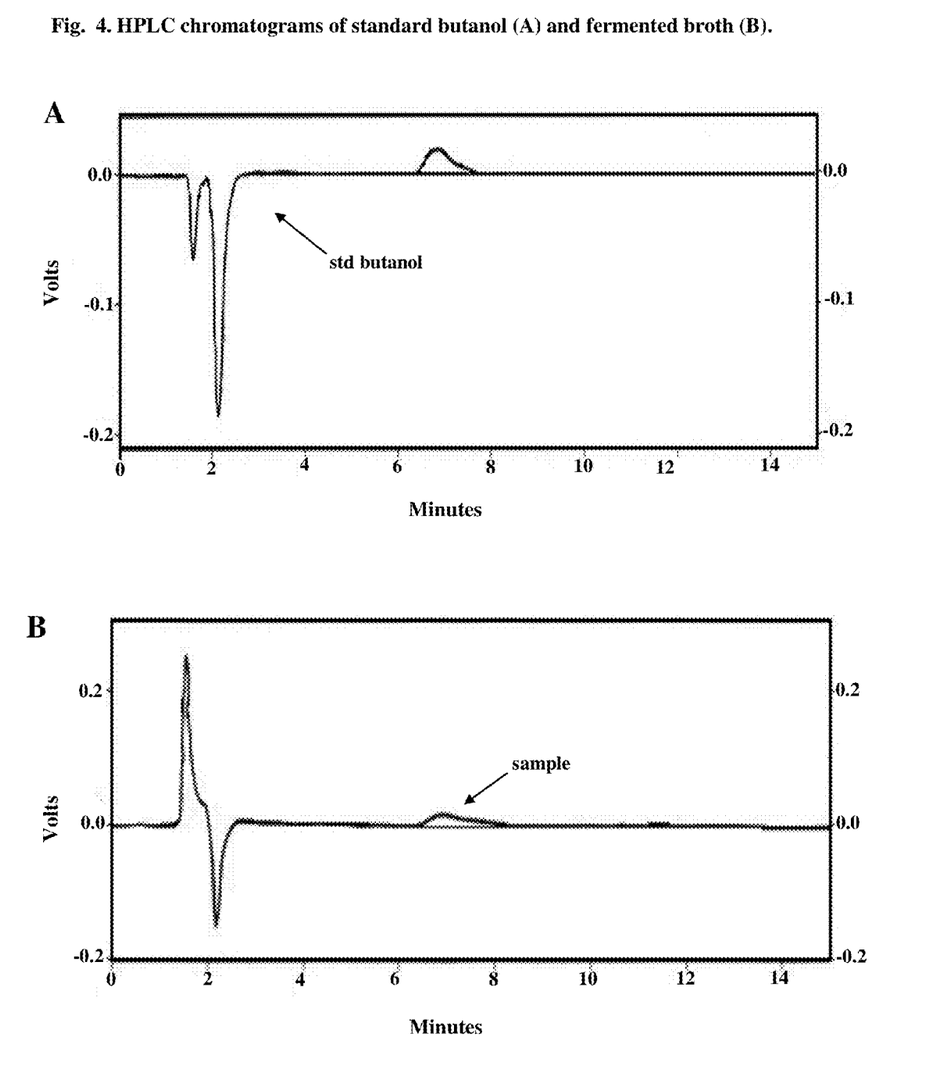
FIG. 4 HPLC chromatograms of std butanol (A) and the fermented broth (B).

The process was further scaled up to 15 L level in a 20 L bioreactor using 7% (w/v) *Jatropha* seed cake and 2% glucose. A butanol titre of 18.6 g/L was achieved in 72 h (FIG. 4 and FIG. 5). The initial sugar was 44 g/L and the final sugar was 4 g/L (FIG. 5). The typical butterfly shift could be observed when the acidogenic phase declined and solventogenic phase commenced.

EXAMPLE 11

Estimation of the Ratio of Acetone, Butanol and Ethanol

The ratio of the solvents produced during the ABE fermentation process was analyzed by HPLC on Rezex organic acid column using 0.1 N $H_2SO_4$ as the mobile phase at a flow rate of 0.6 ml/min using RID detector. Analysis of the fermentation broth on the Rezex organic acid HPLC column revealed that the ratio of acetone:butanol:ethanol was 2.6:6.6:0.8, similar to the ratio obtained in a.typical ABE fermentation.

REFERENCES

Baer, S. H., Biaschek, H. P., Smith, T. L. (1987). Effect of butanol challenge and temperature on lipid composition and membrane fluidity of butanol-tolerant *Clostridium acetobutylicum*. *Appl. Environ. Microbiol.* 53: 2854-2861.

Ezeji, T. C., Qureshi, N., Biaschek, H. P. (2007). Bioproduction of butanol from biomass: from genes to bioreactors. *Curr. Opin. Biotechnol.* 18: 220-227.

Herrera, S. (2004). Industrial biotechnology—a chance at redemption. *Nature Biotechnol.* 22 (6): 671-678.

Jones, D. T., Woods, D. R. (1986). Acetone butanol fermentation Revisited. *Microbiol. Rev.* 50: 484-524.

King, A. J., He, W., Cuevas, J. A., Freudenberger, M., Ramiaramanana, D., Graham, L A. (2009). Potential of *Jatropha curcas* as a source of renewable oil and animal feed. *J. Exp. Bot.* 60: 2897-2905.

Lazaroaie, M. M. (2009). Mechanisms Involved In Organic Solvent Resistance in Gram-Negative Bacteria. *World Acad. Sci, Eng. Technol.* 54:648-658.

Lee, P. C., Lee, W. G., Kwon, S., Lee, S. Y., Chang, H. N. (2000). Batch and continuous cultivation of *Anaerobiospirillum succiniproducens* for the production of succinic acid from whey. *Appl. Microbiol. Biotechnol.* 54: 23-27.

Liang, Y., Siddaramu, T., Yesuf, J., Sarkany, N. (2010). Fermentable sugar release from *Jatropha* seed cakes following lime pretreatment and enzymatic hydrolysis. *Bioresour. Technol.* 101: 6417-6424.

Li, J., Zhao, J. B., Zhao, M., Yang, Y. L., Jiang, W. H., Yang, S. (2010). Screening and characterization of butanol tolerant microorganisms. *Letts. Appl. Microbiol.* 50: 373-379.

Long, S., Long, D. T., Woods, D. R. (1984). Initiation of solvent production, clostridial stage and endospore formation in *Clostridium acetobutylicum* P262. Appl. Microbiol. Biotechnol. 20: 256-261.

Nishino, K., Yamaguchi, A. (2004). Role of histone-like protein H—NS in multidrug resistance of *Escherichia coli.* J. Bacteriol. 186 1423-1429.

Papoutysakis, E. T (2008). Engineering solventogenic *Clostridia. Curr. Opin. Biotechnol.* 19: 420-429.

Parekh, M., Formanek, J., Blaschek, H. P. (1998). Development of a cost effective glucose-corn steep medium for production of butanol by *Clostridium beijerinckii. J. Ind. Microbiol. Biotechnol.* 21:187-191.

Pfromm, H. P., Amanor-Boadu, V., Richard N., Vadlani, P., Madl, R. (2010). Bio-butanol vs. bio-ethanol: A technical and economic assessment for corn and switchgrass fermented by yeast or *Clostridium acetobutylicum. Biomass and Bipenerg.* 34: 515-524.

Qijreshi, N., Saha C. B., Ronald E. H., Bruce, D., Stephen, H., Siq ig, L., Loren, I., Michael J. B., Gaul am, S., Michael, A. C. (2010). Production of butanol (a biofuel) from agricultural residues: Part II—Use of corn stover and switchgrass hydrolysates (2010). *Biomass and Bioener.* 34: 566-571.

Samuelov, $f. S., Lamed, R., Lowe, S., Zeikus, J. G. (1991). Influence of $CO_2$ $HCO_3^+$ levels and pH on growth, succinate production and enzyme activities of *Anaerobiospirillum succiniciproducens. Appl. Environ. Microbiol.* 57: 3013-3019. Sharma, Y., Singh B., Korstad, J. (2010). High yield and conversion of biodiesel from a nonedible feedstock (*Pongamia pinnata*). J. Agric. Food Chem. 58 (1): 242-247.

Sikkema, J., de Bont, J. A., Pool man, B. (1995). Mechanisms of membrane toxicity of hydrocarbons. *Microbiol. Rev.* 59: 201-222.

Sjostrom, E. W (1993). Chemistry: Fundamentals and Application. Academic Press: Orlando. 293 pp.

Tasun, K., Chose, P., Ghen, K. (1970). Sugar determination by DNS method. *Biotech. Bioeng.* 12: 991-992.

Tomas, C. A., Welker, N. E., Papoutsakis, E. T. (2003). Overexpression of groESL in *Clostridium acetobutylicum* results in increased solvent production and tolerance, prolonged metabolism, and changes in the cell's transcriptional program. *Appl. Environ. Microbiol.* 69: 4951-4965.

Tomas, C. A., Beamish, J., Eleftherios (2004). Transcriptional analysis of butanol stress and *Clostridium acetobutylicum. J Bacteriol.* 186(7):2006-2018.

Volherbst-Schneck, K., Sands, J. A., Montenecourts, B. S. (1984). Effect of butanol on lipid composition and fluidity of *Clostridium acetobutylicum* ATCC 824. *Appl. Environ. Microbiol* 47:193-194.

Zainol, N., Rahman, R. A. (2008). Anaerobic cellulose recovery from banana stem waste. Proceedings of the 1st International Conference of the IET Brunei Darussalam Network, 26-27 May.

Thus, while we have described fundamental novel features of the invention, it will be understood that various omissions and substitutions and changes in the form and details may be possible without departing from the spirit of the invention. For example, it is expressly intended that all combinations of those elements and/or method steps, which perform substantially the same function in substantially the same way to achieve the same results, be within the scope of the invention.

We claim:

1. A mutant strain *C. acetobutylicum*, MTCC 5587 obtained by the chemical mutation of a wild strain of *C. acetobutylicum*, ATCC 4259 and having an increased tolerance to butanol as compared to said wild strain.

2. A process of obtaining the mutant strain *C. acetobutylicum*, MTCC 5587 by chemical mutagenesis of *C. acetobutylicum* ATCC 4259 comprising:
    innoculating *C. acetobutylicum* ATCC 4259 culture with an alternate thioglycolate (AT) media for 10 to 14 hours at a temperature in the range of 35 to 40 C;
    centrifuging said culture to obtain a first cell pellet;
    washing said first cell pellet with a citrate buffer;
    decanting said citrate buffer and adding 80 to 120 ul of MNNG (1-methyl-3-nitro-1-nitrosoguanidine), followed by incubation at 27 to 32° C. for 50 to 90 minutes to obtain a mutagenised cell mass;
    centrifuging said mutagenised cell mass to obtain a second cell pellet;
    washing said second cell pellet at least once with an alternate thioglycolate broth to obtain a cell culture;
    screening said cell culture on AT agar plates containing 13 g/L butanol for 12 to 16 hours at 37° C. to obtain said mutant strain *C. acetobutylicum*, MTCC 5587.

3. The mutant strain of claim 1, having a butanol tolerance in the range of 1.5% to 3.5% as compared to said wild strain.

4. The mutant strain of claim 1, wherein the butanol tolerance is associated with increased membrane saturated fatty acid content in the range of 4 to 5% as compared to said wild strain.

5. The mutant strain of claim 1, wherein the butanol tolerance in the mutant strain *C. acetobutylicum*, MTCC 5587 is associated with an increased tolerance to toxic compounds as compared to said wild type.

6. The mutant strain of claim 5, wherein said toxic compound is Rhodamine 6G.

7. A process for production of high yield of butanol from a pretreated biomass using the mutant strain *C. acetobutylicum*, MTCC 5587 having enhanced butanol tolerance, said process comprising fermentation of said pre-treated biomass in the presence of a nutrient medium.

8. The process of claim 7, wherein said biomass is selected from the group consisting of a banana stem, *pongamia* seed cake and *Jatropha* seed cake.

9. The process of claim 7, wherein said nutrient medium is supplemented with sugar.

10. The process of claim 9, wherein said sugar is glucose having 2% concentration.

11. The process of claim 7, wherein said fermentation is carried at a temperature ranging between 33 and 37° C.

12. The process of claim 7 includes further comprising a step of subjecting said pretreated biomass to an acid treatment using 1% to 3% of concentrated hydrochloric acid or sulfuric acid above 100° C. for 1 to 5 hours.

13. The process of claim 12, further comprising a step of neutralization of said acid treated biomass using sodium hydroxide.

14. The process as claimed in claim 7, wherein the butanol tolerance of said mutant strain *C. acetobutylicum*, MTCC 5587 is enhanced from 1.5% to 3.5% as compared to the wild strain *C. acetobutylicum*, ATCC 4259.

15. The process of claim 7, wherein the yield of butanol is up to 19 g/L at 15 L scale using *jatropha* seed cake hydrolysate.

16. The process of claim 7, wherein the yield of butanol is up to 18.0 g/L using banana stem hydrolysate at 50 ml scale.

17. The process of claim 7, wherein the yield of butanol is up to 14.3 g/L using *jatropha* seed cake hydrolysate at 50 ml scale.

18. The process of claim 7, wherein said process yields solvents in the ratio of 2.6:6.6:0.8 of acetone:butanol:ethanol, similar to the ratio obtained in a typical ABE (Acetone, butanol ethanol) fermentation.

\* \* \* \* \*